United States Patent [19]

Anderson

[11] Patent Number: 4,734,423
[45] Date of Patent: Mar. 29, 1988

[54] METHOD OF SOLID CANCER TUMOR TREATMENT USING ISOPROPYLPYRROLIZINE DERIVATIVE

[75] Inventor: Wayne K. Anderson, Williamsville, N.Y.

[73] Assignee: The Research Foundation of State University of New York, Albany, N.Y.

[21] Appl. No.: 804,237

[22] Filed: Dec. 3, 1985

Related U.S. Application Data

[63] Continuation of Ser. No. 378,189, May 14, 1982, abandoned.

[51] Int. Cl.$^4$ .............................................. A61K 31/40
[52] U.S. Cl. ................................................... 514/413
[58] Field of Search ......................................... 514/413

[56] References Cited

PUBLICATIONS

Instruction 14 Screening Data Summary Interpretation and Outline of Current Screen, (National Cancer Institute).
Cancer Treatment Reports, vol. 66, No. 1, Jan. 1982, (Wayne K. Anderson et al.).
Jour. Organic Chemistry, 1977, 42, 599, (Anderson).
Jour. Med. Chemistry, 1977, 20 812, (Anderson).
Jour. Med. Chemistry, 1977, 20 1691, (Anderson).
Journal of Med. Chemistry, 1979, 22, 977, (Anderson).
Jour. Med. Chemistry, 1980, 23 87, (Anderson).
Jour. of Heterocyclic Chemistry, 1980, 17, 513, (Anderson).
Reprint of Arzneimittel-Forschung/Drug Res. 30 (1), 5, 765-767, (1980).
Jour. Med. Chemistry, 1982, 25, 84, (Anderson).
Publication in Jun., 1982, Issue of Cancer Research, (Anderson), Title: The Activity of Bis-Carbamoyloxymethyl Derivatives of Pyrroles and Pyrrolizines Against Human Tumor Xenografts . . .
Grant Applns. CA 22935-01 through -06, Vinylogous Carbinolamine Tumor Inhibitors, (Principal Investigator: W. K. Anderson).
Chemical Structures of Interest to the Division of Cancer Treatment, Apr. 1981, pp. 1, 2, 9 and 19-22, (Author Unknown).
Screening Data Summary, Jun. 11, 1981, (National Cancer Institute).

*Primary Examiner*—Jerome D. Goldberg
*Attorney, Agent, or Firm*—William J. Crossetta; Michael L. Dunn

[57] ABSTRACT

This invention provides a method of providing treatment to a warm blooded animal in need of treatment of a solid cancer tumor comprising administering an effective amount of a isopropylpyrrolizine of the formula:

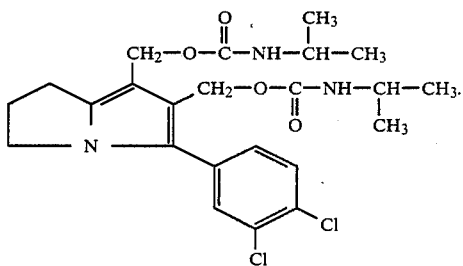

9 Claims, No Drawings

METHOD OF SOLID CANCER TUMOR TREATMENT USING ISOPROPYLPYRROLIZINE DERIVATIVE

The invention described herein was made in the course of work under a grant or award from the Department of Health Education and Welfare.

This application is a continuation of Ser. No. 378,189, filed 5/14/82, now abandoned.

BACKGROUND OF THE INVENTION

This invention relates to a pharmaceutical compound found particularly suitable for inhibiting growth of solid tumors of the colon or breast in warm blooded animals.

PRIOR ART

There has been a continuing search for treatment for solid cancer tumors of the colon or breast in warm blooded animals and especially in human beings. The search for effective, stable and non-toxic treatment materials continues as control of solid cancer tumors has not been particularly well achieved by prior materials. There is a particular need for materials which will be effective against solid tumors of the colon or breast of the colon and breast.

The chemistry of formation of pyrrole compounds has been disclosed in several papers co-authored by Dr. Wayne K. Anderson. Some of these papers also detail the activity of many of the compounds against leukemic cancers and leukemic tumors. These papers concerning the formation of pyrrole compounds are as follows:

1. Anderson, W. K.; Corey, P. F. *J. Org. Chem.* 1977, 42, 559. "1,3-Dipolar Cycloaddition Reactions with Isatin-N-acetic Acids: Synthesis of Dimethyl 9-Oxo-9H-pyrrolo[1,2-a]indole-1,2-dicarboxylates."

2. Anderson, W. K.; Corey, P. F. *J. Med. Chem.* 1977, 20, 812. "Synthesis and Antileukemic Activity of Diacetate and bis(N-Alkylcarbamate) Derivatives of 5-Substituted 2,3-Dihydro-6,7-bis(hydroxymethyl)-H-pyrrolizines."

3. Anderson, W. K.; Corey, P. F. *J. Med. Chem.* 1977, 20, 1691. "Antileukemic Activity of Derivatives of 1-Phenyl-2,5-dimethyl-3,4-bis(hydroxymethyl)-pyrrole Bis(N-methylcarbamate)."

4. Anderson, W. K.; Halat, M. J. *J. Med. Chem.* 1979, 22, 977. "Antileukemic Activity of Derivatives of 1,2-Dimethyl-3,4-bis(hydroxymethyl)-5-phenyl-pyrrole Bis(N-methylcarbamate)."

5. Anderson, W. K.; Halat, M. J.; Rick, A. C. *J. Med. Chem.* 1980, 23, 87. "Synthesis and Antileukemic activity of 1-Methyl-2,5-diphenyl-3,4-bis(hydroxymethyl)-, 1,2,3-Triphenyl-4,5-bis(hydroxymethyl)-, and 1-Methyl-2,3-diphenyl-4,5-bis(hydroxymethyl)pyrrole Bis(N-methylcarbamate)."

6. Anderson, W. K.; McPherson, H. J., Jr.; New, J. S. *J. Heterocycl. Chem.* 1980, 17, 513. "The Synthesis of Polycyclic Benz-Fused Pyrroles."

7. Anderson, W. K.; New, J. S.; Corey, P. F. *Arzneim.-Forsch.* 1980, 30 (I), 765. "Vinylogous Carbinolamine Tumor Inhibitors. 7. Tumor Inhibitory Agents: bis-(N-alkylcarbamate) derivatives of 2,3-dihydro-5-(3',4'-dichlorophenyl)-6,7-bis(hydroxymethyl)-1H-pyrrolizine."

The last paper entitled "Vinylogous Carbinolamine Tumor Inhibitors" is of particular interest as the cyclohexylpyrrolizine derivative of the invention is disclosed therein and indicated as effective for leukemic cancers.

As is well known in the cancer therapy field, the treatment of solid tumor cancers of the colon or breast is more difficult than treatment of leukemic tumor cancers particularly those of the breast or colon. Experience has shown that effectiveness against leukemia is not in any way of assurance of the effectiveness against solid tumors of the colon or breast.

Therefore, there remains a need for compounds suitable for treatment of solid cancer tumors of the colon or breast.

BRIEF DESCRIPTION OF THE INVENTION

An object of this invention is to overcome difficulties of the prior art.

Another object of this invention is to provide improved treatment of solid cancer tumors of the colon or breast.

These and other objects of the invention are generally accomplished by administering sufficient isopropylpyrrolizine derivative having the formula:

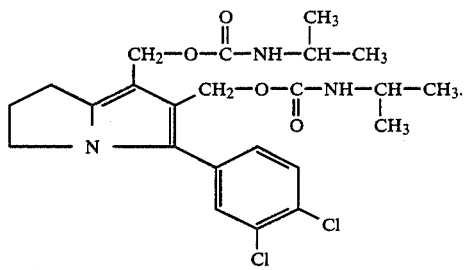

The quantity of the isopropylpyrrolizine derivative sufficient for treatment of cancer tumors of the colon or breast varies depending upon the size of the warm blooded animal involved, upon the type of solid tumor and upon the species of the animal involved. In general for most applications, between about 6 milligrams per kilogram of body weight to about 400 milligrams per kilogram of body weight of the isopropylpyrrolizine derivative is suitable for use in accordance with the method of the invention. In general, large animals require less of any pharmaceutical compound per kilogram of body weight than smaller animals.

MODES OF PRACTICING THE INVENTION

The method of the invention has numerous advantages over prior treatment methods which will become clear from the specification as set forth below. A method of treatment utilizing the isopropylpyrrolizine derivative has a range of activity against tumors. This range extends to a broad group of solid tumors of the colon or breast and also has activity over a broad range of doses. This makes the drug much more suitable for widespread use against different types of tumors of the colon or breast and also lowers the risk margin of a toxic dose being given.

As used herein the term leukemic cancer refers to all cancers or neoplasms of the hemopoietic and immune systems (blood and lymphatic system). The solid tumors as used herein are those of the colon or breast.

The solid tumors are believed more difficult to treat than leukemic cancers as they are slower growing and dense. It is believed that most treatment materials are effective at the time of cell division. The slower growth means fewer cell divisions and fewer opportunities for the treatment compound to affect the cell. The dense mass of tumor does not allow as ready access of the treatment compound to the tumor as the more widely separated cells of the leukemic blood cancers. Therefore, the activity of the compounds of the invention against solid tumors of the colon or breast is unusual and of interest for solid tumor treatment.

The isopropylpyrrolizine derivative may be formed by any satisfactory method. The following is a suitable method:

A solution of L-proline (30 g, 0.26 mol), thymolphthalein (5 mg), and $Na_2CO_3$ (100 g) in water (500 mL) was treated at room temperature with concentrated aqueous NaOH solution until the solution was blue to the thymolphthalein indicator. The stirred solution was cooled to about 10° C. and treated portionwise with a solution of 3,4-dichlorobenzoyl chloride (58.65 g, 0.28 mol) in ether (100 mL) with periodic addition of concentrated aqueous NaOH solution as necessary to maintain the blue color. The reaction mixture was stirred for an additional 10 min after the addition was completed and then extracted with ether (2×150 mL). The aqueous phase was acidified to pH 1 with concentrated HCl and extracted with ethyl acetate (4×250 mL). The combined ethyl acetate solution was washed with brine (150 mL), dried ($Na_2SO_4$), and concentrated in vacuo. The solid residue was crystallized from hot ethyl acetate-petroleum ether (2:1, 300 mL) to give 60.5 g (81%) of N-(3,4-dichlorobenzoyl)proline as fine white prisms. Recrystallization from the same solvents afforded the analytical sample of N-(3,4-dichlorobenzoyl)proline.

A solution of N-(3,4-dichlorobenzoyl)proline (28.813 g 0.1 mol) in acetic anhydride (100 mL) and dimethyl acetylenedicarboxylate (50 mL) was stirred in a flask equipped with a reflux condenser and a gas bubbler to monitor $CO_2$ evolution during the reaction. The mixture was heated to 120° C. over a 15-min period, during which time $CO_2$ evolution occurred at an increasingly rapid rate; the temperature was maintained for 1 h after the rate of gas evolution had substantially decreased. The reaction mixture was concentrated in vacuo and the residue, which solidified on cooling, as twice crystallized from hot methanol (500 mL) to yield 33.35 g (91%) of dimethyl 2,3-dihydro-5-(3,4-dichlorophenyl)-1H-pyrrolizine-6,7-dicarboxylate as analytically pure fine white needles.

A solution of dimethyl 2,3-dihydro-5-(3,4-dichlorophenyl)-1H-pyrrolizine-6,7-dicarboxylate (57.8 g, 0.157 mol) in dry dichloromethane (250 mL) was added dropwise, over a 30-min period, to a mechanically stirred mixture of lithium aluminum hydride (14.04 g, 2.35 equiv) in anhydrous ether (400 ml) heated under reflux. The stirred mixture was heated at reflux for 1 h after the addition was completed and cooled in an ice bath. The excess hydride was decomposed with wet ether and then with water until the salts were white. The mixture was filtered (through sintered glass) and the inorganic residue was washed with several portions (ca. 100 mL) of hot dichloromethane until the total filtrate volume was 1.2 L. The filtrate was concentrated in vacuo to a volume of 500 mL, warmed to boiling, and diluted with slow addition of 350 mL of petroleum ether. Compound 2,3-Dihydro-5-(3',4'-dichlorophenyl)-6,7-bis(hydroxymethyl)-1H-pyrrolizine precipitated as clear, white, chunky prisms (33.8 g); the concentrated mother liquor, after similar treatment, gave an additional 9.71 g of 2,3-dihydro-5-(3',4'-dichlorophenyl)-6,7-bis(hydroxymethyl)-1H-pyrrolizine to a total yield of 89%.

2,3-dihydro-5-(3',4'-dichlorophenyl)-6,7-bis(hydroxymethyl)-1H-pyrrolizine Bis(isopropylcarbamate). A solution of 2,3-dihydro-5-(3',4'-dichlorophenyl)-6,7-bis(hydroxymethyl)-1H-pyrrolizine (6.244 g, 0.02 mol) and triethylamine (0.5 mL) in dichloromethane (45 mL) was treated with isopropyl isocyanate (7 mL, ca. 10 equiv) and refluxed for 1.5 h. The mixture was concentrated to dryness in vacuo and the off-white residue was crystallized from ethyl acetate-isopropyl ether to give about an 81% yield of 2,3-dihydro-5-(3',4'-dichlorophenyl)-6,7-bis(hydroxymethyl)-1H-pyrrolizine Bis(isopropylcarbamate).

Another method believed suitable for formation of the cyclohexylpyrrolizine derivative of the invention is set forth below. This method is considered lower in cost as pyrrolidone is utilized rather than proline to produce the dimethyl 2,3-dihydro-5-(3',4'-dichlorophenyl-1H-pyrrolizine-6,7-dicarboxylate intermediate. While it is illustrated with the ethyl 2-(3,4-dichlorophenyl)-2-bromoethanoate other halogens or hydrocarbon groups also could be utilized.

2-Pyrrolidone

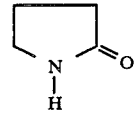

1

Ethyl 2-(3,4-dichlorophenyl)-2-bromoethanoate

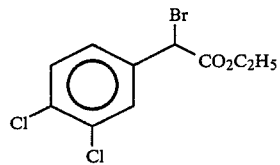

2

Treat 1 with an appropriate base such as sodium hydride and, in situ, treat the anion with 2. Hydrolyze resulting ester 2 with aqueous base (or acid) to give 3.

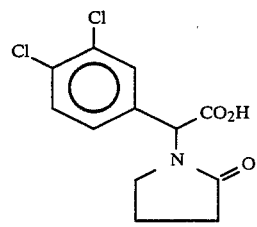

3

Then treat 3 with dimethyl acetylenedicarboxylate and acetic anhydride to give dimethyl 2,3-Dihydro-5-(3',4'-dichlorophenyl)-1H-pyrrolizine-6,7-dicarboxylate.

Then proceed as first set forth to the compound of the invention from this intermediate.

The general synthesis of these compounds is set forth in the paper entitled "Synthesis and Antileukemic Activity Of 5-Substituted 2,3-Dihydro-6,7-bis(hydroxymethyl)-1H-pyrrolizine Diesters" *J. Med. Chem.*, 1977, Vol. 20, No. 6, pp. 812–818.

Any suitable dosage may be given in the method of the invention. The type of and the amount of dosage will vary widely depending on the species of the warm blooded animal, body weight and tumor of the colon or breast treated. Generally, a dosage of between about 6 milligrams per kilogram of body weight and about 400 milligrams per kilogram of body weight is suitable. Generally, the dosage in man for solid cancer tumors of the colon or breast is lower than for small warm blooded mammals such as mice.

The method of treatment may be any suitable method which is effective in treatment of the particular solid tumor of the colon or breast which is under treatment. A method of applying an effective amount also varies depending on the tumor of the colon or breast being treated. It is believed that treatment by intravenous application formulated with an appropriate carrier to facilitate intravenous application will be the suitable method of administering the cyclohexylpyrrolizine derivative in man.

The following tests demonstrate the surprising effectiveness of the treatment of the invention.

EXAMPLES

Tumor cells were inoculated ip (intraperitoneal) into male $CDF_1$ mice, unless otherwise noted, in the B16, and colon tumor 26 assays. The tumors in the $CD8F_1$ and colon tumor 38 assays were implanted sc (subcutaneously) in male $CDF_1$ and female $BDF_1$ mice, respectively. Tumor cells were injected iv (intravenously) into female $BDF_1$ mice in the Lewis Lung tumor (LL). Six to ten animals were used in each test group, and 40 untreated animals were used in the control groups. In the survival models (B16, colon tumor 26, and LL) as well as in the tumor weight (estimated from tumor diameters) models ($CD8F_1$ and colon tumor 38), results are expressed as a percentage of the test animal evaluation (T) compared to that for the controls (C) and are reported as %T/C; these values are based on all mice, not just dying mice.

The test animal evaluation (T) for mice in survival models when compared to the control group (C) of mice provides a comparison of the number of the mice surviving the test with treatment as opposed to the test group where treatment was not given. Therefore, a high % T/C number indicates the treatment was effective in survival tests. In the tumor weight tests, the test animal evaluation (T) provides an estimate of the tumor weight in treated mice and compares it to the estimated tumor weight in the untreated control mice. In the tumor weight test a low % T/C indicates effective treatment as the tumors on treated mice are smaller than tumors on the untreated control mice. The test compounds were administered ip as suspensions; the vehicles were distilled water-Tween 80.

The dose in any given assay is defined as toxic if any of the test animals die within the first 5 days of the test, unless otherwise specified (Tables 1-5). Test animal weight changes are noted in parentheses, and these data may be regarded as an indication of continuing drug toxicity. The weight change data are expressed as T-C (test animal weight change minus control animal weight change, in g).

TABLE 1

| Dose (mg/kg) | −% T/C in colon 26 tumor* |
|---|---|
| 200 | Toxic |
| 100 | 55(−4.0) |
| 50 | >233(−1.3) |
| 25 | >233(−1.6) |
| 12.5 | >233(+0.7) |
| 6.25 | >233(−0.2) |

*Tumor homogenate, diluted 1:100, was inoculated ip into female $BDF_1$ mice. 1 dose of the compound was given 24 hrs after tumor inoculation, and another was given 4 days later. Values in parentheses = T-C, weight change in g.

TABLE 2

| Dose (mg/kg) | −% T/C in $CD8F_1$ *Mammory Solid Tumor |
|---|---|
| 400 | Toxic |
| 200 | Toxic |
| 100 | 6(−3.9) |
| 50 | 50(−3.2) |
| 25 | 69(−1.8) |
| 12.5 | 52(−1.1) |

*Tumor homogenate containing approximately $5 \times 10^6$ cells was inoculated sc into male $CD8F_1$ mice; 5 doses of a compound were given ip beginning 24 hrs after tumor inoculation and, thereafter, every 7 days. Dose was defined as toxic if all test animals failed to survive the 30-day test. Values in parentheses = T-C, in g.

TABLE 3

| Dose (mg/kg) | −% T/C in colon 38 tumor*+ |
|---|---|
| 200 | 0(−7.9) |
| 100 | 34(−2.2) |
| 50 | 131(−2.1) |
| 25 | 114(−2.4) |
| 12.5 | 129(−3.7) |
| 6.26 | 138(−2.3) |

*A tumor fragment was implanted sc in female $BDF_1$ mice; 1 dose of a compound was given ip 2 days after tumor implantation, and another was given 7 days later. Dose was defined as toxic if all test animals failed to survive the 20-day test. Values in parentheses = T-C, in g.

TABLE 4

| Dose (mg/kg) | −% T/C in B16-Solid Tumor*+ |
|---|---|
| 200 | Toxic |
| 100 | 60(−4.3) |
| 50 | 146(−3.1) |
| 25 | 310(−2.5) |
| 12.5 | 222(−2.0) |
| 6.25 | 169(−2.14) |

*Tumor homogenate (0.5 ml, prepared from a homogenized mixture of 1 g of tumor and 10 ml of balanced salt solution) was inoculated ip; 9 daily doses of a compound were given ip beginning 24 hrs after tumor inoculation. Values in parentheses = T-C, in g.

Female $B6C3F_1$ mice were used in this assay.

TABLE 5

| Dose (mg/kg) | −% T/C in LL-Solid Lung Tumor* |
|---|---|
| 200 | 40(−5.8) |
| 100 | 50(−4.9) |
| 50 | 109(−2.9) |
| 25 | 125(−2.1) |
| 12.5 | 119(−2.2) |
| 6.25 | 101(−1.2) |

TABLE 5-continued

| —% T/C in LL-Solid Lung Tumor* |
|---|
| Dose (mg/kg) |
| 3.12 | 97(−1.3) |

*Ascitic fluid containing approximately 10⁵ cells was injected iv into female BDF₁ mice; 9 daily doses were given ip, beginning 24 hrs after tumor inoculation. Values in parentheses = T-C, in g.

The administration of the compound of the invention resulted in cures of the B-16 tumor in the instance of three of the ten mice that received the 25 milligram per kilogram of body weight. Four of the ten animals that received a dose of 200 milligrams per kilogram of body weight were cured of the CD8F₁ mammary tumor. It can also be seen that the compound of the invention was particularly effective against the colon tumor 38 and the colon tumor 26. The compound of the invention was active against the colon tumor 26 increased life span 133% which was the maximum possible percent increase in lifespan in this 100-day test, at all doses in the range of 6.25-50 mg/kg. The compound of the invention also produced cures in seven (7) or ten (10) animals that received doses of 12.5 and 25 mg/kg. Taken together, the results indicate a high level of effectiveness against a wide range of solid tumors. The compounds of the invention are more active against solid tumors than presently used compounds for treating such tumors.

While the specification only illustrates the effectiveness of the compounds against tumors implanted in mice, it is also within the invention to utilize the treatment for all warm blooded animals, particularly treatment of mammals is contemplated.

What is claimed is:

1. A method of providing treatment to a warm blooded animal in need of treatment of a solid cancer tumor of the colon or breast comprising parenterally administering to said warm blooded animal an effective solid cancer tumor inhibiting amount of an isopropyl-pyrrolizine of the formula:

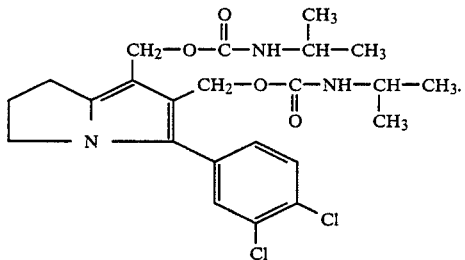

2. A method of inhibiting the growth, in an warm blooded animal, of a solid cancer tumor of the colon or breast susceptible to a isopropylpyrrolizine of the formula:

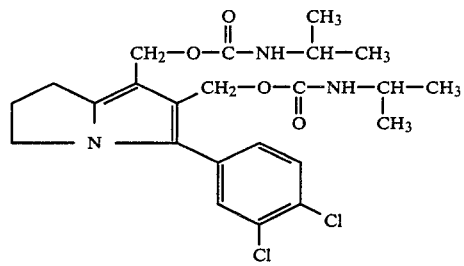

comprising parenterally administering to said warm blooded animal, in vivo, an effective solid cancer tumor inhibiting amount of said isopropylpyrrolizine.

3. The method of claim 2 wherein the quantity of said isopropyl pyrrolizine administered is between about 6 and about 400 milligrams per kilogram of body weight of the warm blooded animal.

4. The method of claim 2 wherein said warm blooded animal is a mammal.

5. The method of claim 4 wherein said isopropylpyrrolizine is administered intravenously.

6. The method of claim 4 wherein said isopropylpyrrolizine is administered subcutaneously.

7. The method of claim 4 wherein an effective amount of said isopropylpyrrolizine is administered intraperitoneally.

8. The method of claim 4 wherein said effective amount of isopropylpyrrolizine is administered with a carrier material.

9. A pharmaceutical preparation adapted for parenteral administration in a warm blooded animal to inhibit the growth of a solid cancer tumor of the colon or breast, in vivo, comprising, per dosage unit, a solid cancer tumor inhibiting effective non-toxic amount, within the range of 6 to about 400 milligrams per kilogram of body weight of the warm blooded animal being administered, of a isopropylpyrrolizine of the formula:

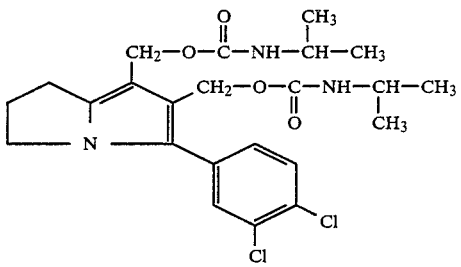

and a pharmaceutical diluent.

* * * * *